(12) United States Patent
Charlton

(10) Patent No.: US 8,801,433 B1
(45) Date of Patent: Aug. 12, 2014

(54) DENTAL INSTRUMENT

(71) Applicant: Daniel Charlton, Del Mar, CA (US)

(72) Inventor: Daniel Charlton, Del Mar, CA (US)

( * ) Notice: Subject to any disclaimer, the term of this patent is extended or adjusted under 35 U.S.C. 154(b) by 0 days.

(21) Appl. No.: 13/784,642

(22) Filed: Mar. 4, 2013

(51) Int. Cl.
*A61C 3/00* (2006.01)

(52) U.S. Cl.
USPC .............................................. 433/141; 433/30

(58) Field of Classification Search
USPC .................................. 433/141, 147, 30; 30/321
See application file for complete search history.

(56) References Cited

U.S. PATENT DOCUMENTS

| | | | | |
|---|---|---|---|---|
| 163,578 A * | 5/1875 | Cogswell | ......................... | 433/30 |
| 649,234 A * | 5/1900 | Chiavaro | ....................... | 433/147 |
| 656,300 A * | 8/1900 | Perry | ........................... | 433/141 |
| 736,101 A * | 8/1903 | Hough | ......................... | 433/147 |
| 827,507 A * | 7/1906 | Crawford | ..................... | 433/147 |
| 904,990 A * | 11/1908 | Powers | ........................ | 433/102 |
| 3,609,864 A * | 10/1971 | Bassett | ........................... | 30/261 |
| 4,100,677 A * | 7/1978 | Jeff | ................................. | 30/321 |
| 4,788,976 A * | 12/1988 | Dee | ................................ | 606/167 |
| 5,055,106 A * | 10/1991 | Lundgren | .................... | 606/167 |
| 5,431,671 A * | 7/1995 | Nallakrishnan | ............... | 606/167 |
| 2012/0244486 A1* | 9/2012 | Solomon | ........................... | 433/3 |

\* cited by examiner

*Primary Examiner* — Ralph Lewis
(74) *Attorney, Agent, or Firm* — Donn K. Harms

(57) ABSTRACT

A dental instrument having a first member with an axial passage engageable with a removable second member. Rotationally engageable dental tools engageable at a first end of the first member, are fixed in a radial position around their axle by the distal end of the second member engaged within the axial passage. The dental instrument allows for the tools to be from a kit featuring a plurality of different tools, each of which is engageable to the axle, and rotatably adjustable for holding in a fixed position by the second member.

13 Claims, 3 Drawing Sheets

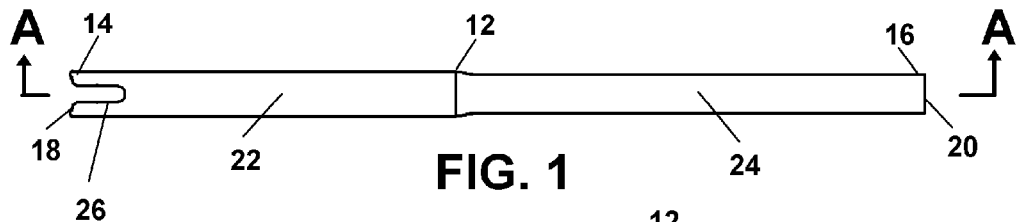
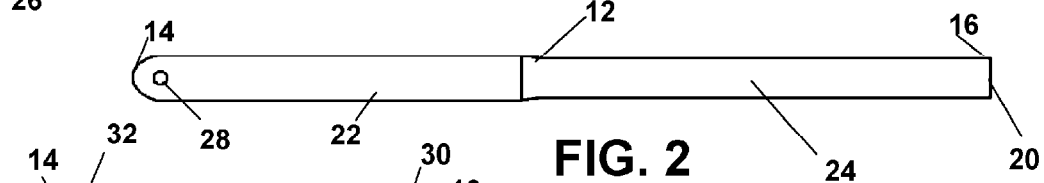
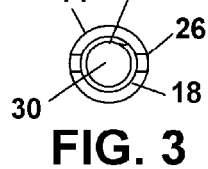
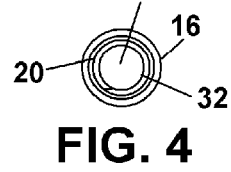
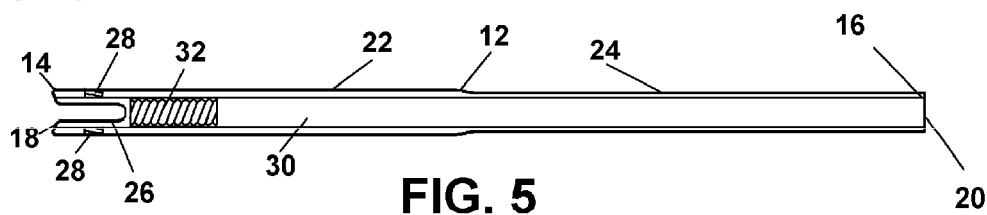
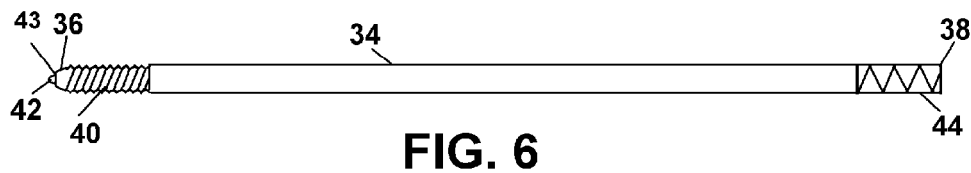
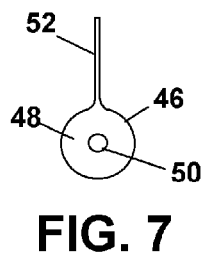
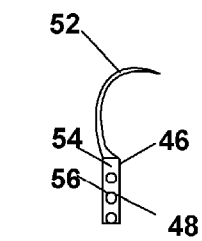
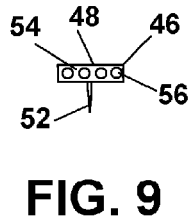
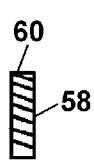

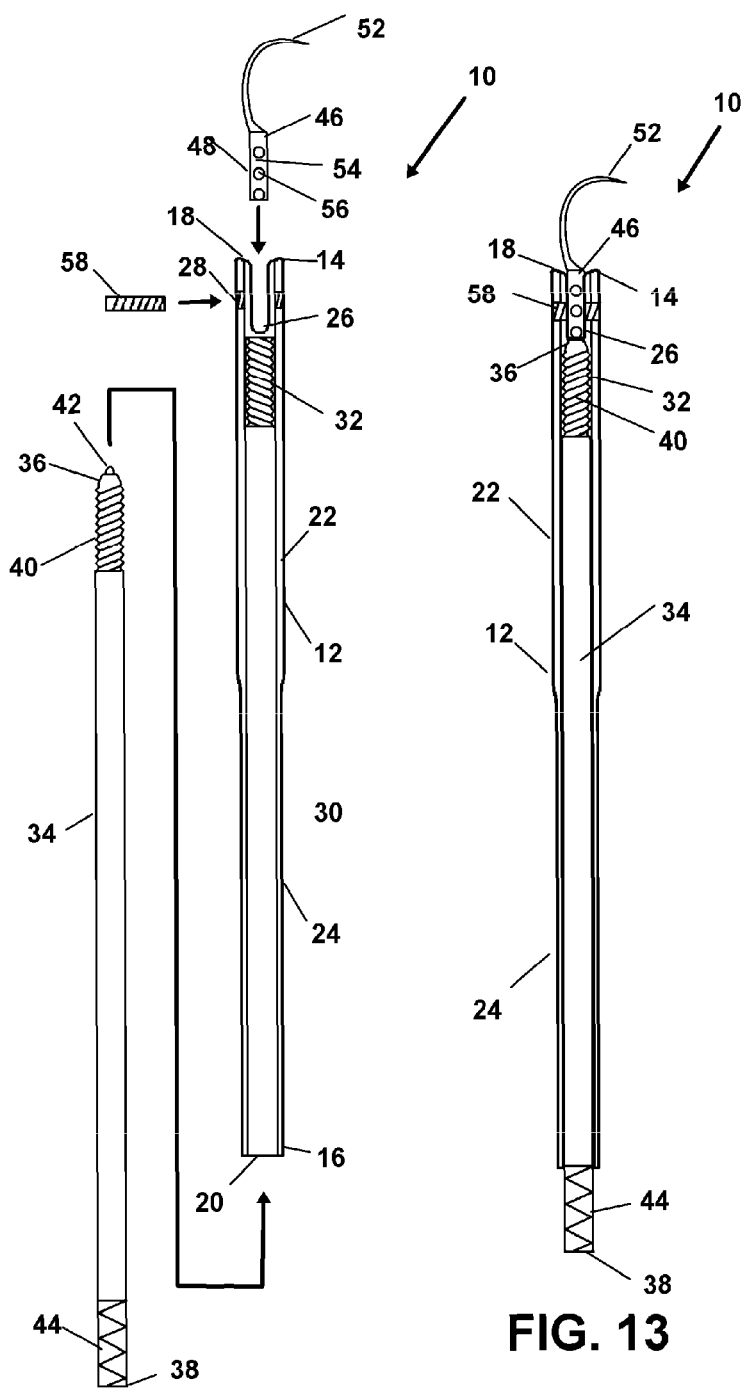
FIG. 12
FIG. 13
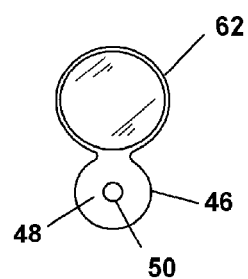
FIG. 14
FIG. 15
FIG. 16

DENTAL INSTRUMENT

BACKGROUND OF THE INVENTION

1. Field of the Invention

The present invention relates to dental instruments. More particularly, the invention relates to a dental instrument having a handle employable with any one of a plurality of engageable tools or instrument heads. The handle has a distal end which is formed to operatively engage the heads which are rotationally positionable by the user, to a customized configuration of the assembled device yielding a head-positioning for employment during the dental task at hand. The handle, so configured, can engage any of the plurality of instrument heads which are adapted to perform particular dental procedures. The kit of heads also can include a sharpener for the heads.

2. Prior Art

Dentists and dental professionals employ a wide range of instruments when providing dental treatment to patients. Many instruments are handheld and thus require precise positioning and movement skills of a dental professional to manipulate correctly. Such tools generally have handles with tooled tips at a distal end and are commonly employed to examine, manipulate, restore and remove teeth, tooth materials, plaque, adhesives, and other tasks on adjacent and surrounding oral structures.

Such instruments typically comprise such an elongated handle with a specific instrument head engaged at one end in a fixed engagement and adapted to perform the dental task intended. Conventionally, they are formed from stainless steel or other material which can necessitate, and survive, sterilization (for example in an autoclave) for a proper reuse. Examples of dental instruments and tools configured as head types include mirrors, probes, retractors, burs, excavators, scalpels, burnishers, pluggers, curettes, forceps, elevators, chisels, and many others.

Conventionally, such instrument handles employ head portions which are unitarily formed to a single structure, or otherwise permanently engaged to a distal end to form a single instrument. This construction provides a sturdy one-piece structure and is desired in that manner because of the significant force sometimes communicated to the handle by the dental professional in the removal or forming of dental structures which might bend the instrument were it not formed in a sturdy fashion. However, as a result, many dental professionals must maintain a large quantity of instruments, and because of multiple daily patients, and sterilization requirements, most dental offices will typically stock a multiple of each type instrument.

As such, a large amount of space is needed to store and clean these instruments which can be quite difficult in small offices or locations with little room accommodating the storage and sterilization requirements. Further, the need to maintain a large quantity of such instruments, many in duplication or multiple copies, is a constant and significant cost to dental practices.

In addition, many professionals choose to sharpen their tools in house. This requires sharpening apparatuses which are conventionally bulky, as they must be configured to accommodate the instrument handle and head portion. Again accommodating for such sharpening, requires a significant amount of office space, which may not be available for all users. Even if such space is available, commercial rental rates to procure such space which will not accommodate paying clients is significant.

Further, because the use of such tools is as much an art as an acquired skill, different dental professionals want the tool end of their instruments, bent, sharpened, and other wise configured to their individual configurations. Such individualized configurations may not be preferred by other dental professionals participating in the same venue. This can result in further expense for duplication and replacement of such tools to accommodate individual user desire.

As a consequence, the employment of handles with removable heads and tools, has risen as one potential solution to some of the aforementioned problems. An example is shown in U.S. Pat. No. 634,732 to Ivory, as well as others which teach the employment of dental instruments which have heads or tools which may be removably engageable to the handles. Means for such removable engagement can include instrument heads employing threaded collars for engagement to threads operatively positioned at a distal end of the handles, as well as others means for removable engagement.

In such prior art as Ivory, the user can removably engage and interchange various head types as needed for the task at hand. Therefor the user may stock fewer handles along with a plurality of various instrument heads, noting that the heads are typically smaller than the handles and therefor easier to store and sanitize in large quantities. In many instances the instrument heads are simply discarded and replaced after use.

One skilled in the art can easily ascertain the many downfalls which exist with conventional means for removable engagement of instrument heads to handles. Firstly, as noted, such instruments frequently require a large amount of force be communicated to accomplish their task. Converse to imparting increased force is the need for placement and positioning in very precise movements in the delicate environment of a patient's mouth. As a consequence, many such handles with engageable heads to function as tools, will buckle or move in their engagement under such force.

Further, the dental professional must employ the various dental instruments, while manipulated in their hands, to position the head and tool portion thereof, at various angles in the crowded mouth during use. Once in proper angled alignment with work to be done, the tool then is manipulated often with twisting or curving motions, and under force. Such motions with the tool end of the handle engaged in work, frequently causes a conventional threaded engagement, to unscrew and disengage, or to move a small or large amount, which is not only frustrating to the dental professional, but can be dangerous to the patient.

As such the users must take great care to ensure the instrument head remains securely engaged to the handle in order to reduce the risk of the head inadvertently becoming loose or disengaged during use. Absent such caution, such dental instruments even in the hand of skilled professionals can potentially cause serious injury to the patient or to the user. Frequently, instruments taught by prior art fail to provide adequate force-resistant engagement and assurance to the user they will not move or dismount during use.

U.S. Pat. No. 4,672,964 to Dee et. al teaches means for rotatable frictional engagement of a scalpel to a handle providing angular adjustment of the scalpel. This allows the user to vary the attack angle of the instrument head and therefor allow employment of the device at various angles. However, this and similar devices suffer from the downfalls of conventional threaded removable engagement, and frictional engagement means, to engage the tool itself to the distal end of the handle, and thus are fraught with potential problems noted above.

As such, there is a continuing unmet need, for a dental instrument handle device, providing multiple instrument heads all adapted with means for removable and rotationally positionable engagement of instrument heads to the handle. Such a device should provide means for a secured positive engagement of the head onto the handle which will handle the large amount of force imparted to dental tools, yet still allow the user to employ it in the delicate movements required. Further, preferably such a device should provide a means for rotational engagement of the head portion with the distal end of the handle portion, which allows the user to adjust the angle of the tool on the head to then be secured at such a desired positioning for individual patient mouth structures and work thereon. In addition, such a device should advantageously be providable to the user in a kit form, wherein one handle component is configured at a working end for operative operational engagement with any of a plurality of removably engaged instrument heads. Finally, such a device should be provided with a sharpening component which remedies the aforementioned need for excess rental space.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art. The device achieves the above noted goals through the provision of a dental instrument handle device, configured with means for removable engagement of a plurality of heads and a rotational positionable engagement of the head so engaged, in a manner to yield a dental tool capable of the delicate manipulations and high force imparted by processionals. To that end, the device provides a means to securely position the head in a desired rotational angular position, relative to the handle axis, once engaged to the handle.

In general, the device is comprised of two concentrically engaged and coaxially aligned handle components. The first component, also referred to as the outer component or handle component, is an elongated member of substantially circular cross section having a first end, a second end, and an axial passage defined by an interior surface communicating between apertures located at the respective first and second ends. The first component or outer component may be formed from stainless steel rod, tubing or other material which may be sterilized and will withstand the forces involved in the procedure to be performed.

The first end includes means for a rotational engagement for any one of a plurality of instrument head components. In a preferred such rotational engagement, the first end includes a longitudinal slot, extending from the first end into the handle and towards the second end. The slot is preferably positioned inline with the axis running through the axial passage of the first component and is configured to receive a proximal end of an instrument head therein.

The preferred means for rotational engagement of the proximal end within the slot includes a removable threaded locking pin which is engaged into a threaded aperture formed at or near the first end of the first component normal to the longitudinal axis. The pin can be communicated through the threaded aperture and into a through-aperture formed in the proximal end of the head component providing a pivot thereof.

The second component (also referred to as the inner component) is formed of an elongated member of substantially circular cross section, slightly smaller than a cross section of the axial passage, and having a first end and a second end. The second component may also be formed from a length of stainless steel rod or other metal material. The exterior surface of the second component includes a threaded portion starting at the first end, and extending a distance towards the second end of the second component.

Additionally, the first end of the axially locatable second component, includes a projection extending from a distal surface, which is configured for cooperative engagement within detents formed in the proximal end of the head components, described shortly below. The second end of the axially located second component, preferably includes a gripping surface portion for opposing finger and thumb of the user's hand, as can be provided by knurling the exterior surface.

In use, the aperture at the second end of the first component and the axial passage thereof is sized to receive the elongated member forming the second component in concentric and coaxially aligned engagement. In accordance with a first preferred mode, the interior surface of the axial passage at or near the first end of the first component, includes an interior threaded portion. This interior threaded portion is configured to threadably engage a cooperatively threaded exterior threaded portion of the first end of the second component when in an concentric engagement.

In use, as the two components in axial alignment are threaded together, the first end of the second component extending toward the opposite end of the axial passage, advances further toward the first end of the first component until the projection engages within at least one detent formed in a row on the exterior of instrument head. This engagement provides securement of the instrument head and locks rotational position and angle thereof relative to the axis of the first component, extending from the of the first component.

In all preferred modes, the device is configured for removable engagement with various members of a plurality of head components. Briefly, the tool provided by the head components may comprise any dental tool from a group of dental tools including mirrors, probes, retractors, burs, excavators, scalpels, burnishers, pluggers, curettes, forceps, elevators, chisels, and others are also anticipated.

The head components are preferably configured with the specific tool engaged at a first end, and a cooperative means for engagement to the handle at a second end. In accordance with a first preferred mode, the cooperative means for engagement includes an end having a projection with a curved or substantially circular endwall, extending from the first end of the tool component. The projection is preferably circular in cross section, and includes a front surface, rear surface, and a circumferential side surface. There are included a plurality of detents, disposed in a spaced relationship from each other on the circumferential side surface which extend radially inward into the body of the projection. These detents are configured in shape and inward dependence for a contacting engagement with the area of the projection on the first end of the second component as described above.

In yet another mode, the device includes a kit which is providable to the user comprising the dental instrument handle device, a plurality of removably engageable instrument heads, and a sharpening apparatus. The sharpening apparatus is preferably configured to engaged the removable instrument heads, and therefor can be sized smaller than conventional sharpening apparatuses which are configured to engage the handle and head. Further, the sharpening apparatus may include a instrument head mount which is configured with an engagement means similar to that of the handle device. As such the user will be familiar with the means to engaged the heads to the sharpening apparatus and can insure a proper sharpening.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of this invention to provide a user configurable dental tool formed of a head portion and handle, which provides for a secure mount of a user chosen tool at the distal end of a handle and at a user chosen angle.

Additional objects, features, and advantages of the invention will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings:

FIG. 1 shows a first side view of a preferred mode of the outer handle component of the dental instrument handle device.

FIG. 2 shows a second side view of outer component of FIG. 1.

FIG. 3 shows a first end view of the outer component of FIG. 1.

FIG. 4 shows a second end view of the outer component of FIG. 1.

FIG. 5 shows a cross sectional view of the outer component of FIG. 1 shown along line AA of FIG. 1.

FIG. 6 depicts a first side view of a preferred mode of the inner component of the dental instrument handle device.

FIG. 7 shows a front view of a first particularly preferred mode of a removably engageable instrument head component having a sickle scaler tool end.

FIG. 8 depicts a side view of the instrument head of FIG. 7.

FIG. 9 shows a bottom view of the instrument head of FIG. 7.

Figure 17:
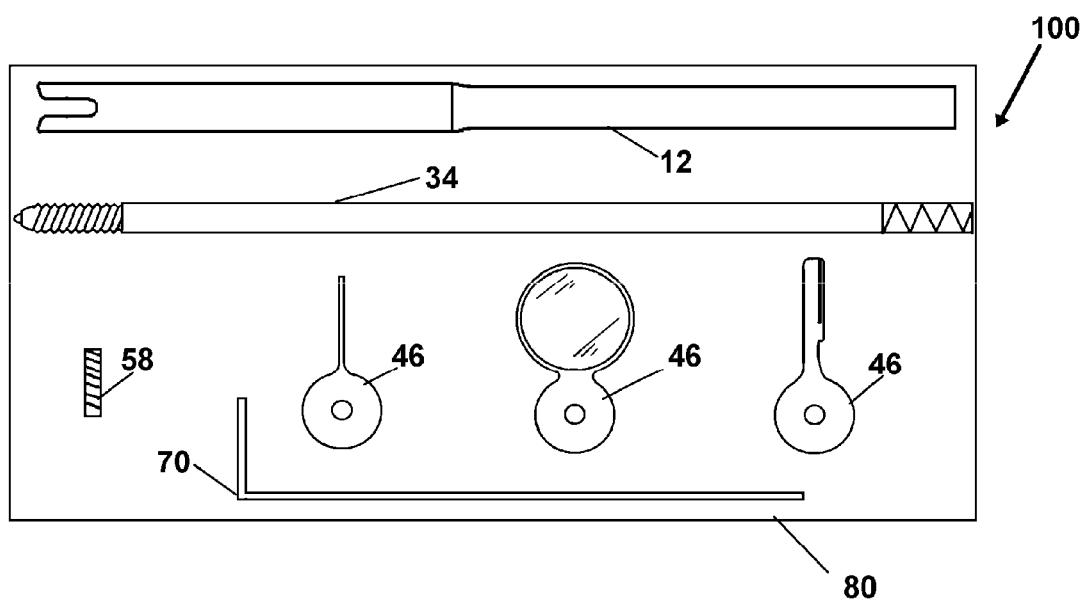

FIG. 10 a side view of the threaded hinge pin of the device.

FIG. 11 shows an end view of the hinge pin showing a hex type engagement socket.

FIG. 12 shows an exploded view of the dental instrument device of the present invention.

FIG. 13 shows cross sectional view of the device in the as used mode.

FIG. 14 shows a depiction of the rotational engagement of the instrument head to the handle.

FIG. 15 shows another preferred mode of a removably engageable instrument head having a mirror tool.

FIG. 16 shows still another preferred mode of a removably engageable instrument head having a scalpel handle.

FIG. 17 shows a kit comprising the inner and outer handle components, a plurality of instrument heads, threaded locking pin, and wrench.

DETAILED DESCRIPTION OF THE PREFERRED EMBODIMENTS OF THE INVENTION

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Now referring to drawings in FIGS. 1-17, wherein similar components are identified by like reference numerals, there is seen in FIG. 1, FIG. 2, FIG. 3, FIG. 4, and FIG. 5 views of the outer component 12 of the dental instrument handle device 10. The various components of the device 10 disclosed herein can be formed of conventional materials such as stainless steal, metal, metal alloys, and plastic, however can be formed of any material suitable for the purposes set forth in this disclosure.

The outer component 12 formed by a first member having a first end 14 and a second end 16. A first aperture 18 communicating through the first end 14 communicates with an axial passage 30 which runs through the first member forming the outer component 12, to a second aperture 20 at the second end 16. The axial passage 30 communicating between the first and second ends of the outer component 12 is dimensioned to translatabley receive an inner handle component 34 shown in FIG. 6 which is formed by a second member. The second member forming the outer component 34 may be translated and inserted along the axial passage 30 toward the first end 14, after insertion of its distal end, through the second aperture 20.

A first exterior surface portion 22 of the first member forming the outer component 12 is configured with means for an enhanced a grip between the opposed thumb and finger of a user with surfacing which may be knurled, textured, or otherwise surfaced with a suitable gripping surface capable of surviving sterilization and heat. Preferably provided also is a second exterior surface portion 24 may have a smooth finish as is seen in conventional dental instruments.

As can be seen in the figures, the first end 14 of the first elongated member forming the outer component 12 includes an elongated slot 26, extending through the axial passage 30 and opposing cutouts 29 in the sidewall defining the axial passage 30 of the outer component 12. The slot 26 depends into the first end 14 a distance towards the second end 16, which is determined by the depth of the cutouts 29 into the sidewall from the distal edge of the outer component.

Shown in the exploded and assembled views of FIG. 12 and FIG. 13, the slot 26 is configured to cooperatively engage with one end of the removably engageable instrument heads 46. In the cross sectional view of FIG. 5, the axial passage 30 of the first member has at least one threaded portion 32, formed into the interior of the sidewall defining the passage 30, herein shown in a particularly preferred location, disposed adjacent the first end 14.

Positioning of the threaded portion 32 adjacent to the first end 14, allows for the threaded exterior portion 40 adjacent to the distal end of the second member forming the inner component 34, to engage the threaded portion 32, in a cooperative threaded engagement, immediately adjacent to the first end 14. This threaded engagement holds the second member forming the inner component 34 in its coaxial engagement, with its proximal end extending past the second end 16, by preventing a translation of the inserted second member forming the inner component 34, in a direction away from the first end 14.

Just as important, this threaded engagement centers the projection 42 extending from the distal edge 43 of the inner component 34 aligned with the axis of the axial passage. It thus provides a means for a centered communication of the projection 42 at the distal end of the inner component 34, through the first aperture 18, at the first end 14.

The first aperture 18 disposed at the first end 13 is preferably sized just larger in circumference, than the exterior circumference of the projection 42 to provide a contacting engagement of the first aperture 18, around the circumference of the projection 42. This contacting engagement, provides a means for maintaining the projection 42, extremely stable when force traverse to the axis of the first member forming the outer component 14, is communicated to the projection 42.

This contacting engagement is particularly preferred because when the projection 42 engages with an instrument head 46 of a removably engaged tool, this stable positioning of the projection 42 provided by the contacting engagement, with the projection 42 engaged with the instrument head 46, holds the tool securely in position. This allows the user to put great pressure on the tool being used while at any engaged angle while it is being used, which is most important in dental surgery for the safety of the patient and success of the procedure.

Further, the engagement of the threaded exterior portion 40 with the threaded portion 30, fixes the projection 42 in axial alignment with the axis running through the center of the axial passage 30, such that it remains stationarily centered which is important to maintain the instrument heads 46 stabilized, and in a fixed angle relative to the axis, and substantially unmoving. As noted such a three dimensional secure engagement is especially important during surgery in the mouth when the user exerts high force to the device 10 while using it in a patient's mouth.

The mating threads have a pitch of the threaded exterior portion 40 and threaded portion 32 which are configured to provide translation with a stable engagement and axial positioning, of the interior component within the axial passage 30 adjacent to the first end 14 of the outer component 12. Such a pitch can be for instance a UNF fine thread for the diameter of the inner component. A cessation of the threads of the threaded portion 32 results in a tight and compressive engagement of the two sets of threads when the inner component 34 is rotated.

This tight compressive engagement of the threads of both components, upon rotation of the inner component 34 until the threaded exterior portion 40 threads reach the end of the threaded portion 32, in addition to maintaining the projection 42 axially centered with the axial passage 30, provides a means to prevent movement and inadvertent loosening of the inner component 34 adjacent to the first end 14. This prevents substantially any movement of the projection 42, while engaged into and against the surface forming the detents 56 formed on the individual instrument heads 46 device 10 in the as-used mode of FIG. 13. Ideally the dimensions of the exterior surface of the projections 42 mirror the surface defining the detents 56, which results in a compressive contact of the projection 42 against the surface of the detent 56 thereby enhancing the stabilization of the instrument head 46 within the slot.

As shown in FIG. 6, the elongated member forming the inner component 34 may also be formed of conventional materials such as stainless steel however it may be formed of any material suitable for the purposes set forth in this disclosure. The inner component 34 is shown in FIG. 6, with the first end 36 extending to an opposing second end 38 of the inner component 34. As noted, the first end 36 includes at least one or a plurality of distal projections 42, which are employed to fixedly engage into the detents 56 formed in the instrument heads 46. As shown, the first end 36 of the second component has a threaded exterior portion 40, which is as noted, configured for threaded engagement with the threaded portion 32 of the passage 30 when the inner component 34 is inserted into the passage 30 of the first component 12 and rotated.

The second end 38 of the inner component 34 also includes a gripping portion 44 about its circumferential exterior surface. This is provided to enhance engagement between the user's thumb and finger, to allow for the user to achieve an enhanced compressive engagement of the threads as noted above. The means for enhanced engagement for a user's opposing thumb and finger may be provided by knurling the exterior surface, or any other suitable means known in the art.

FIG. 7, FIG. 8, and FIG. 9 show views of a first preferred mode of a removably engageable instrument head 46 and the configuration thereof to engage with the projection 42. The head 46 includes an engagement member 48, which is shown with a tool end 52 configured to function as a sickle scaler tool. It is noted however that other modes of the instrument head 46 can include a tool end 52 extending from an engagement member 48 formed as other dental tool types, for example having a tool end such as those shown in FIG. 15 and FIG. 16 having mirror tool end 62 and scalpel handles end 64 respectively.

It is additionally noted and anticipated that orientation and disposition of the mirror 62 or other tool end 52 extending from attachment with an engagement member 48 may be modified as needed. For example in another modes the mirror 62 can be configured perpendicular to the plane of the engagement member 48, or essentially at any relative angle deemed suitable by the designer. Other tool types are well known in the art and need not be pictured, but can include tool ends 42 formed as probes, retractors, burs, excavators, burnishers, pluggers, curettes, forceps, elevators, and chisels. Further the tool ends 52 noted herein may be provided in kit form, with substantially identical engagement members 48, configured for rotational engagement within the slot, and compressioned engagement with a projection 42, with each having a different said tool end 52 configuration thereon to allow engagement of any member of the kit, with a handle of the device 10.

Particularly preferred, the engagement member 48 has a circumferential sidewall 54 into which a plurality of detents 56 extend inward and are formed to substantially mirror the dimensions and shape of the exterior surface of the projection 42 to provide for the compressive engagement between the two surfaces thereof. However it is noted that in other modes the sidewall 54, and the projection 42, may be employed, so long as the two cooperatively engage when the inner component is rotated. Such mating engagements can instead comprise a plurality of serrations or other recesses dimensioned for a complimentary engagement with a projection 42 extending from the inner component 34.

The member 48 also include a substantially central aperture 50 which in use is operatively aligned with the threaded aperture 28 of the outer handle component 12, and a threaded hinge pin 58 is communicated therethrough. FIGS. 10 and 11 show side and end views of the hinge pin 58. The endwall 60 of the hinge pin 58 may include a hex type engagement cavity, for receiving a conventional allen wrench to allow the user to threadably engage the pin 58 in a communication through the through aperture and into the threaded aperture 28.

Referring again to the exploded and assembled views of FIG. 12 and FIG. 13, the user engages the head 46 at the first end 14 of the outer component 12 via the hinge pin 58 thorough the engagement member 48. The aperture 50 through the engagement member 48 portion of the head 46 is preferably sized in very close tolerance but with clearance within the engaged aperture 50 for the pin 58 such that the head 46 may rotate freely thereon once engaged.

The rotational angular position of the head 46, relative to the axis of the passage 30, can be selectively positioned by the user and customized to their liking by threading the inner component 34, into the passage 30 of the outer component and advancing the projection 42 to an engagement with the one of the detents 56 of the head 46. The threaded engagement described above allows the user to impart a compressive force of the projection 42 and surrounding distal end of the inner component 34 against circumferential edge and detent 56 and therefor maintain and insure a solidly secured positioning of the head 46 at the chosen angle.

As such, shown in FIG. 14 the available rotational positions of the head 46 is only limited to the number of detents 56 formed in the circumferential sidewall 54. It should be noted that the radius of the circular end of the engagement member 48, thickness of the sidewall 54, width and/or distance of depending of the slot 26, and the length and/or size of the projection 42, and number and size of the detents 56 can be adjusted to yield more angular positions, larger tools, and other accommodations and thus are of the designers choice and should not be considered limited by the depiction.

FIG. 17 shows a particularly preferred kit 100 of the invention comprising the inner and outer components 12, 34, threaded locking pin 58 and optional wrench 70, and a plurality of instrument heads 46 which as already noted may be provided in a kit. The kit can be provide in a sterile sealed container 80, or any other suitable means for maintaining the device and the heads 46 sterile prior to use. A instrument head sharpening apparatus may also be provided. Alternatively the heads 46 may be provided in sealed containers 80, and engaged to pre-sterilized handles to allow users to customize their instrument and either dispose of or reuse the heads 46.

This invention has other applications, potentially, and one skilled in the art could discover these. The explication of the features of this invention does not limit the claims of this application; other applications developed by those skilled in the art will be included in this invention.

It is additionally noted and anticipated that although the device is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A dental instrument, comprising:
    a first member, having an axial passage running therethrough defined by an internal surface of a sidewall, said axial passage communicating between a first aperture at a first end of said first member to a second aperture at a second end of said first member;
    an axle positioned at or adjacent to said first end of said first member, said axle configured for a removable rotational engagement with a dental tool;
    a second member having a proximal end and extending to distal end;
    a projection extending along a center axis of said second member, from a distal edge at said distal end of said second member;
    said second member postionable through said first aperture to an engaged position in a coaxial engagement within said axial passage of said first member;
    means for engagement of said second member to said first member to maintain said second member in said engaged position;
    said projection, with said second member in said engaged position, extending through said first aperture to a tip, said tip of said projection forming a contact with a surface of said dental tool positioned in a said rotational engagement;
    said contact providing means for fixing a radial position of said dental tool in a said rotational engagement with said axle, whereby a user can engage a said dental tool to said axle, and rotate said tool thereon to a user chosen position, and render said tool to fixed said radial position upon said axle, by positioning said second member to said engaged position;
    a notch extending across said second end of through openings formed in opposing portions of said sidewall at said first end of said first member;
    said axle removably engageable with opposite portions of said sidewall to a mounted position, in a direction traverse to said notch;

said tool when positioned to said rotational engagement having a circumferential surface facing toward said first end of said first member;

at least one recess formed in said circumferential surface; and said tip of said projection formed in a cooperative shape to said recess, whereby said tip is positionable to said contact with said recess to render said tool to a said fixed radial position.

2. The dental instrument of claim 1, additionally comprising:

a plurality of sequentially positioned recesses formed in said circumferential surface; and said tip of said projection positionable to a said contact with any of said plurality of recesses formed in said circumferential surface, each respective said contact yielding a different one of a plurality of fixed radial positions of said tool upon said axle.

3. The dental instrument of claim 2 wherein said means for engagement of said second member to said first member to maintain said second member in said engaged position comprises:

threads formed on said first member engageable by mating threads formed on said second member.

4. The dental instrument of claim 3 additionally comprising:

said threads formed on said first member being upon said inner surface; and said mating threads formed on said second member being upon a circumferential surface thereof.

5. The dental instrument of claim 4 additionally comprising:

a slot formed in said first end of said first member;

said threads formed on said first member being upon said inner surface adjacent to said slot; and said circumferential surface for said mating threads being at or adjacent to said distal end of said second member.

6. The dental instrument of claim 5 additionally comprising:

said projection having a circumference sized to contact a circumferential edge defining said aperture when said second member is positioned to said engaged position.

7. The dental instrument of claim 6 additionally comprising:

said dental tool obtainable from a kit of dental tools, each dental tool of said kit configured for a said rotational engagement with said axle.

8. The dental instrument of claim 1 wherein said means for engagement of said second member to said first member to maintain said second member in said engaged position comprises:

threads formed on said first member engageable by mating threads formed on said second member.

9. The dental instrument of claim 8 additionally comprising:

said threads formed on said first member being upon said inner surface; and said mating threads formed on said second member being upon a circumferential surface thereof.

10. The dental instrument of claim 9 additionally comprising:

a slot formed in said first end of said first member;

said threads formed on said first member being upon said inner surface adjacent to said slot; and said circumferential surface for said mating threads being at or adjacent to said distal end of said second member.

11. The dental instrument of claim 10 additionally comprising:

said projection having a circumference sized to contact a circumferential edge defining said aperture when said second member is positioned to said engaged position.

12. The dental instrument of claim 11 additionally comprising:

said dental tool obtainable from a kit of dental tools, each dental tool of said kit configured for a said rotational engagement with said axle.

13. The dental instrument of claim 1 additionally comprising:

said dental tool obtainable from a kit of dental tools, each dental tool of said kit configured for a said rotational engagement with said axle.

* * * * *